(12) United States Patent
Sellars et al.

(10) Patent No.: US 9,010,178 B2
(45) Date of Patent: Apr. 21, 2015

(54) EROSION TESTING ASSEMBLY

(75) Inventors: Christopher Sellars, Derby (GB); Andrew Hewitt, Derby (GB)

(73) Assignee: Rolls-Royce PLC, London (GB)

(*) Notice: Subject to any disclaimer, the term of this patent is extended or adjusted under 35 U.S.C. 154(b) by 421 days.

(21) Appl. No.: 13/357,028

(22) Filed: Jan. 24, 2012

(65) Prior Publication Data
US 2012/0192629 A1 Aug. 2, 2012

(30) Foreign Application Priority Data
Feb. 2, 2011 (GB) .................................. 1101746.4

(51) Int. Cl.
*G01N 3/56* (2006.01)
*D06F 57/00* (2006.01)
*D06F 58/10* (2006.01)

(52) U.S. Cl.
CPC ................ *D06F 57/00* (2013.01); *D06F 58/10* (2013.01); *G01N 3/567* (2013.01)

(58) Field of Classification Search
CPC ........... G01N 7/00; G01N 3/567; G01N 3/56; G01N 17/00
USPC .............................................. 73/86, 431, 866
See application file for complete search history.

(56) References Cited

U.S. PATENT DOCUMENTS

| | | | | |
|---|---|---|---|---|
| 2,628,456 A * | 2/1953 | Berg | ................................ | 451/87 |
| 2,723,498 A * | 11/1955 | Hastrup et al. | .................. | 451/88 |
| 2,907,200 A * | 10/1959 | Roberts et al. | ...................... | 73/7 |
| 3,229,498 A * | 1/1966 | Oakes | .................. | 73/7 |
| 3,479,857 A * | 11/1969 | Bloxsom, Jr. et al. | ........ | 73/12.11 |
| 3,566,670 A * | 3/1971 | Rindal | ............................. | 374/45 |
| 3,709,026 A * | 1/1973 | Rhodes et al. | ............... | 73/12.11 |
| 3,978,761 A * | 9/1976 | Sosinski | .......................... | 411/5 |
| 4,045,915 A * | 9/1977 | Gilbert et al. | .................. | 451/90 |
| 4,212,138 A * | 7/1980 | Hutchison | ....................... | 451/90 |
| 4,232,487 A * | 11/1980 | Brown | ............................ | 451/88 |
| 4,375,740 A * | 3/1983 | Brown | ............................ | 451/88 |
| 4,395,850 A * | 8/1983 | Brown | ............................ | 451/90 |

(Continued)

FOREIGN PATENT DOCUMENTS

CN 201314887 Y 9/2009
CN 201716245 U 1/2011

(Continued)

OTHER PUBLICATIONS

"2002 Research and Technology Report NASA TM-2003-211990", NASA/Glenn Research Center, Mar. 2003, pp. 40-41.*

(Continued)

*Primary Examiner* — David A Rogers
(74) *Attorney, Agent, or Firm* — Oliff PLC

(57) ABSTRACT

An erosion testing assembly adapted to test an abradable surface of a component, the testing assembly including: a shroud attachable to the component; the shroud being adapted to receive an erosion gun. The present disclosure also relates to a method of testing an abradable surface of a component, wherein the method includes: attaching a shroud to the component; connecting an erosion gun to the shroud; and testing the abradable surface with the erosion gun. The present disclosure may also relate to a method of testing an abradable surface of a component, wherein the method includes: using the component; and testing a portion of the abradable surface with an erosion gun after use of the component.

3 Claims, 3 Drawing Sheets

(56) References Cited

U.S. PATENT DOCUMENTS

| | | | |
|---|---|---|---|
| 4,418,730 A * | 12/1983 | McMath | 141/207 |
| 4,735,364 A * | 4/1988 | Marchant | 239/690.1 |
| 5,010,693 A * | 4/1991 | Hatch | 451/90 |
| 5,069,260 A * | 12/1991 | Shea | 141/292 |
| 5,343,733 A * | 9/1994 | Nakagawa et al. | 73/7 |
| 5,526,680 A * | 6/1996 | McLaughlin | 73/54.01 |
| 5,531,634 A * | 7/1996 | Schott | 451/39 |
| 5,998,242 A * | 12/1999 | Kirkpatrick et al. | 438/127 |
| 6,192,763 B1 | 2/2001 | Cartwright | |
| 6,230,544 B1 * | 5/2001 | Matsubara et al. | 73/7 |
| 6,390,898 B1 | 5/2002 | Pieper | |
| 7,347,768 B1 * | 3/2008 | Drew | 451/38 |
| 7,959,983 B1 * | 6/2011 | Farrar et al. | 427/422 |
| 7,988,376 B2 * | 8/2011 | Todd | 401/186 |
| 8,047,048 B2 * | 11/2011 | Jenkins et al. | 73/7 |
| 8,510,874 B2 * | 8/2013 | Duboc | 4/255.11 |
| 2005/0235763 A1 * | 10/2005 | Blewett et al. | 73/866 |
| 2010/0242580 A1 | 9/2010 | Nelson et al. | |

FOREIGN PATENT DOCUMENTS

| | | |
|---|---|---|
| EP | 0 204 187 A1 | 12/1986 |
| GB | 1 415 579 | 11/1975 |
| GB | 2 021 450 A | 12/1979 |
| GB | 2 144 537 A | 3/1985 |
| JP | A-8-62114 | 3/1996 |
| SU | 1019286 A | 5/1983 |

OTHER PUBLICATIONS

"TM 55-2835-209-23—Engine Assembly, Gearbox Assembly Gas Turbine", Dept. of the Army, Jan. 28, 1992.*
Search Report issued in European Patent Application No. 12 15 2252 dated Nov. 20, 2012.
Search Report issued in British Patent Application No. GB1101746.4 dated Apr. 8, 2011.

* cited by examiner

EROSION TESTING ASSEMBLY

This invention relates to an erosion testing assembly and particularly but not exclusively relates to an erosion testing assembly for components of a gas turbine engine.

Abradable linings may be used in gas turbine engines, for example, on surfaces facing a labyrinth seal, which may be positioned on the inside of the compressor case and shrouds to accommodate relative radial movements. Such abradable seals may be subjected to an erosive environment, for example, as dust and grit accelerated in the gas stream impacts onto the abradable seals. The abradable lining or coating may be reduced in thickness by this erosion, which may in turn compromise the sealing performance, as the clearance gap between the rotating components (compressor blade or drum fin) is increased.

To ensure adequate erosion performance, erosion testing may be undertaken on abradable test samples, e.g. prior to approval. Presently, such testing is undertaken using a prior art erosion test apparatus, an example of which is shown in FIG. 1. The prior art erosion test apparatus 10 comprises an erosion gun 12, e.g. a grit blaster, which is fed with grit from a grit hopper 16 and air from an air supply 18. The air supply 18 propels grit from the grit hopper 16 towards a specimen held in holder 20 and positioned at a set orientation in front of the erosion gun 12. The grit hopper 16, air supply 18, erosion gun 12 and holder 20 may be housed in a sealed cabinet 14. The performance of the abradable coating may be assessed in terms of the time taken to erode a set volume of the abradable coating.

Recent service experience has highlighted the need to assess the erosion performance of abradable coatings following service exposure, as some coatings are exhibiting signs of early life erosion failure. This information may be used to determine the remaining erosion life of an abradable coating for a given service exposure. This may in turn also be used to set as manufactured and aged erosion performance limits for abradable coatings.

However, the prior art erosion testing apparatus is only suitable for testing coatings on relatively small substrates (e.g. approximately 2"×2" or 5 cm×5 cm), and therefore unsuitable for assessing the erosion performance of abradable coatings once applied to a component, for example in a gas turbine. The option of cutting the component into the small substrates required is not desirable as this then renders the component scrap.

The prior art erosion test apparatus also relies on the test sample having a flat surface that acts as a datum from which the depth of erosion can be measured. It is however likely that the surface of service run abradable coatings are not flat, since there may have been some material loss as a result of blade incursion, spallation or erosion.

The present disclosure therefore seeks to address these issues.

According to a first aspect of the present invention there is provided an erosion testing assembly adapted to test a surface, e.g. an abradable surface, of a component, the testing assembly comprising: a shroud attachable to the component; the shroud being adapted to receive an erosion gun.

The component may be part of a device. The component may be part of a turbomachine. The component may be part of a gas turbine. The shroud may be attachable to the component in situ within the device.

The erosion testing assembly may further comprise a connector, e.g. a resilient connector, adapted to connect the shroud to the component. The shroud may comprise a lip for hooking onto the component. The connector may comprise the lip for hooking onto the component. The shroud may comprise protrusions adapted to be received in corresponding recesses in or adjacent to the component. The connector may comprise the protrusions adapted to be received in the corresponding recesses in or adjacent to the component.

The shroud may comprise an opening adapted to receive the erosion gun. The shroud may further be adapted to receive a profile measuring device. The opening may also be adapted to receive the profile measuring device.

According to a second aspect of the present invention there is provided a method of testing a surface, e.g. an abradable surface, of a component, wherein the method comprises: attaching a shroud to the component; connecting an erosion gun to the shroud; and testing the surface, e.g. with the erosion gun.

The method may further comprise: using the component; and testing a portion of the abradable surface after use of the component, e.g. in its intended application.

The method may further comprise measuring the surface profile of the abradable surface before and/or after testing, e.g. with the erosion gun. The method may further comprise replacing the erosion gun with a profile measuring device.

According to a third aspect of the present invention there is provided a method of testing a surface, e.g. an abradable surface, of a component, wherein the method comprises: using the component; and testing a portion of the surface with an erosion gun after use of the component.

According to a fourth aspect of the present invention there is provided a testing assembly adapted to test a surface, e.g. an abradable surface, of a component, the testing assembly comprising: a shroud attachable to the component; the shroud being adapted to receive: an erosion tester; and/or a profile measuring device.

The erosion tester may comprise an erosion gun. The profile measuring device may comprise a laser profile measurement device.

Advantageously, the erosion testing assembly of the present disclosure may enable erosion testing of any size component, whereas the prior art is limited to substrates approximately 2"×2" or 5 cm×5 cm in size. Furthermore, the erosion testing assembly of the present disclosure may connect to a specific component or part of a component. The erosion testing assembly of the present disclosure may also ensure accurate location of the test area and/or shielding of the surrounding parts of the component. The erosion testing assembly of the present disclosure may also be portable and may be applied to a component in situ within a device.

For a better understanding of the present invention, and to show more clearly how it may be carried into effect, reference will now be made, by way of example, to the accompanying drawings, in which:—

FIG. 2a shows a sectional side view of a testing assembly according to an example of the present disclosure and FIG. 2b shows a further sectional view corresponding to section A:A as shown in FIG. 2a;

Figure 1:
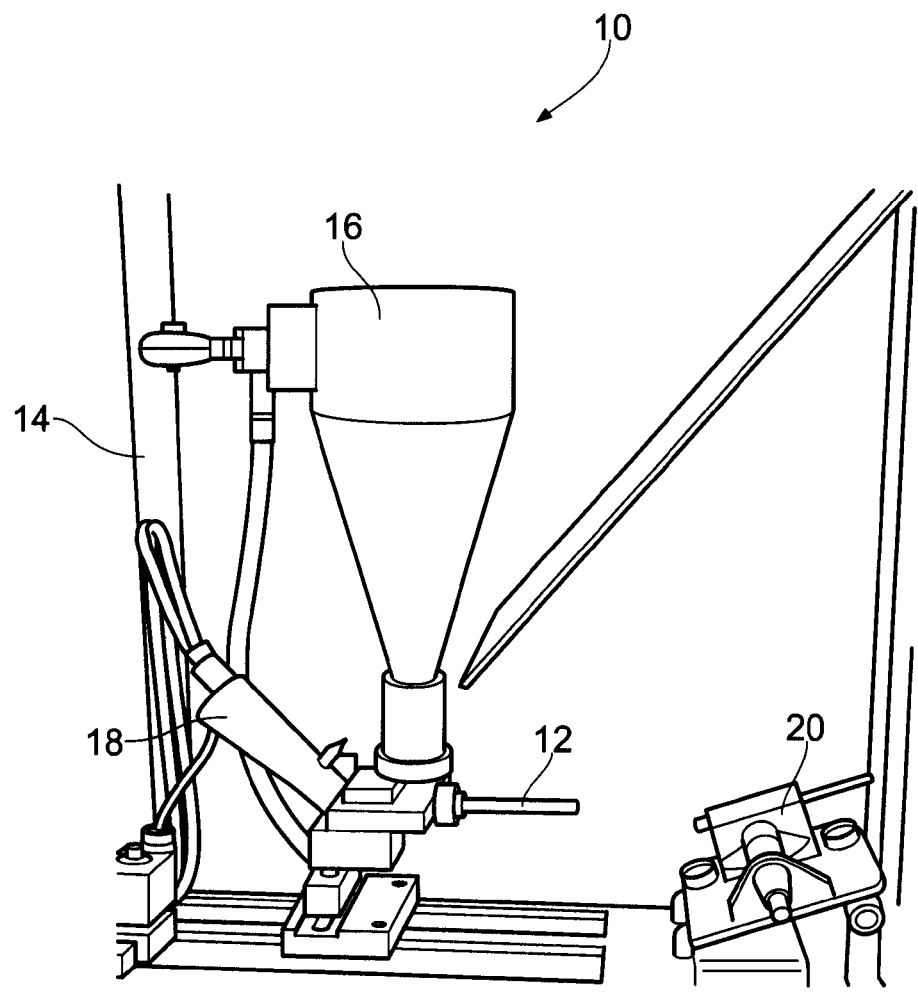
FIG. 1 shows a prior art erosion test assembly.
Figure 2A:
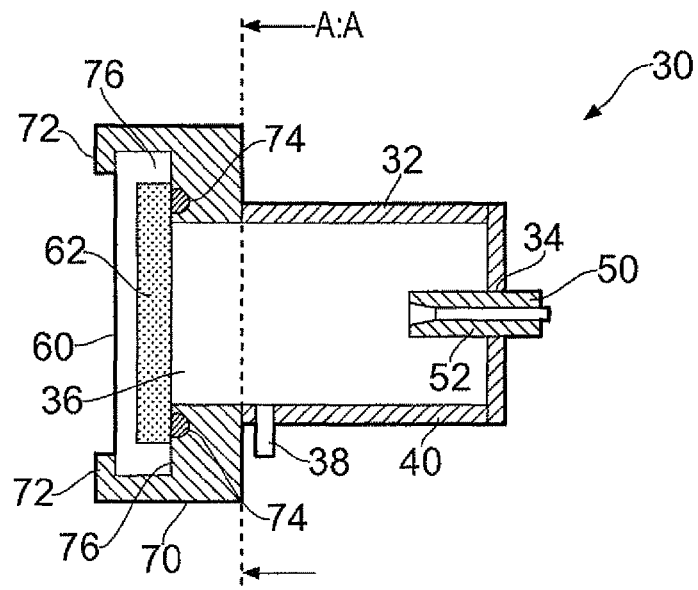
Figure 2B:
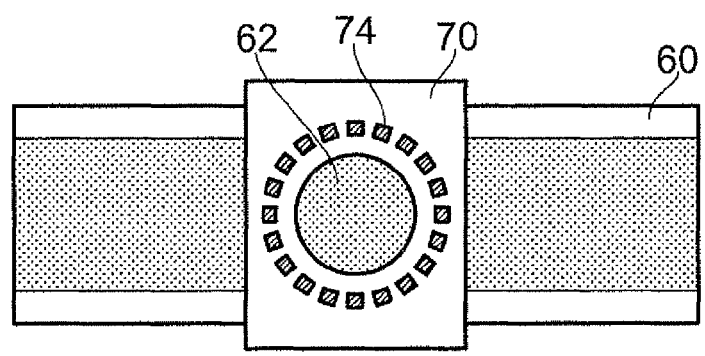

With reference to FIGS. 2a and 2b, an erosion testing assembly 30 according to an example of the present disclosure, may be adapted to test at least of portion of an abradable surface, liner or coating 62 of a component 60. The erosion testing assembly 30 may comprise a shroud 32, which may be attachable to the component 60. The shroud 32 may comprise a first opening 34 and a second opening 36. The first and second openings 34, 36 may be disposed at opposite ends of the shroud 32. The shroud may be substantially tubular, e.g. with the first and second openings 34, 36 disposed at opposite ends of a tubular section 40. The shroud 32 may be circular in cross-section at a first end adjacent to the first opening 34 and, as shown in FIG. 2b, the shroud 32 may be rectangular, e.g. square, in cross-section at a second end adjacent to the second opening 36.

The first opening 34 may be adapted, e.g. shaped and/or sized, to receive an erosion gun 50. The erosion gun 50 may be removable from the shroud 32, e.g. by extraction from the first opening 34. The erosion gun 50 may comprise a barrel 52, which may be located within first opening 34. The barrel 52 may correspond in shape and size to the first opening 34. The erosion gun 50 may propel grit and/or air through the barrel 52 and towards the abradable surface 62 of the component 60. The erosion gun may be connected to a source of grit and a source of compressed air (not shown).

The shroud 32 may attach or connect to the component 60 such that the second opening 36 of the shroud 32 is adjacent to the abradable surface 62 of the component 60. The grit and/or air may therefore flow from the first opening 34, by virtue of the erosion gun 50, through the shroud 32, through the second opening 36 and thence to the abradable surface 62 of the component 60. The erosion gun 50 may therefore cause erosion of the abradable surface 62, but the shroud 32 may shield other components and/or the remainder of the component 60 from the grit and hence any erosion. The shroud 32 may comprise a third opening 38. The third opening 38 may be in a side-wall of the shroud 32. The third opening 38 may permit the flow of air and/or grit out of the shroud 32, for example once the air and/or grit has hit the abradable surface 62 and fallen to the side-wall of the shroud 32.

The erosion testing assembly 30 may further comprise a connector 70 adapted to connect the shroud 32 to the component 60. The connector 70 may be part of the shroud 32. The connector 70 may act as an interface between the remainder of the shroud 32 and the component 60. The connector 70 may be shaped at a first end to receive at least a portion of the component 60 and may be shaped at a second end to connect to the remainder of the shroud 62. The connector 70 may convert from the tubular geometry of the remainder of the shroud 32 to the geometry of the component 60. In the example shown, the connector 70 converts the circular geometry of the tubular section 40 to the rectangular geometry of the connector 60.

The connector 70 may comprise a lip 72 adapted to hook around the component 60. Accordingly, the lip 72 may secure the connector 70 and hence erosion testing assembly 30 to the component 60. The lip 72 may be provided on opposite sides of the connector 60 and the lip may overhang corresponding sides of the component 60. The connector may be resilient, for example the connector may be made from rubber or any other resilient material.

The connector 70 may form part of the shroud 32 and may connect to the remainder of the shroud 32. The connector 70 may be removably affixed to the shroud 32. One or more connectors may be provided, e.g. to connect to components with different geometries. The connectors may be interchangeable.

The connector 70 may comprise an abutment surface 76, which may abut the component 60. The connector 70 may seal against the component 60. For example, the connector may comprise a seal 74, which may seal against the component 70. The seal 74 may be provided on the abutment surface 76 of the connector 70. The seal 74 may comprise an O-ring and the seal 74 may be made from a resilient material, e.g. rubber.

Figure 3:
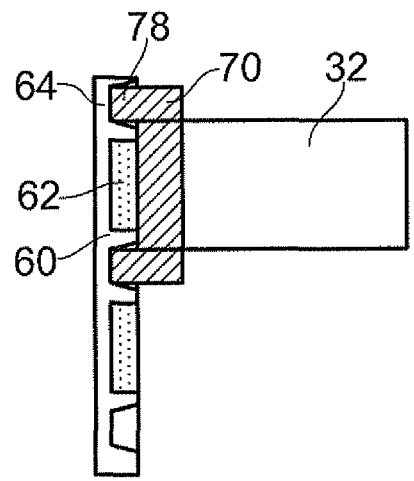
FIG. 3 is a side view of a testing assembly according to an alternative example of the present disclosure.

With reference to FIG. 3, the connector 70, in an alternative example, may comprise one or more protrusions 78. The protrusions 78 may be adapted to be received in corresponding recesses 64 in or adjacent to the component 60. The protrusions 78 may engage the recesses 64 so as to secure the erosion testing assembly to the component 60. The protrusions 78 may be shaped and sized to fit and/or engage the recesses 64.

Figure 4:
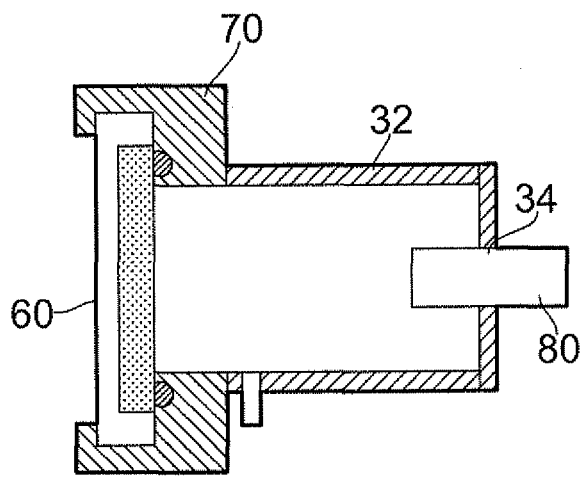
FIG. 4 is side view of the testing assembly according to the example of the present disclosure receiving a profile measuring device.

With reference to FIG. 4, the erosion gun 50 may be replaced with a profile measuring device 80. The first opening 34 may also be adapted, e.g. shaped and/or sized, to receive the profile measuring device 80. Alternatively, the erosion gun 50 or profile measuring device 80 may fit in the first opening 34 by virtue of an intermediate spacer (not shown) to adapt the shape and size of the erosion gun 50 or profile measuring device to the first opening 34. The profile measuring device 80 may comprise a laser profile measuring device. The component 60 may be part of a device. For example, the component may be part of a turbomachine and/or a gas turbine. The shroud 32, e.g. via the connector 70, may be attachable to at least a portion of the component in situ within the device. For example, the erosion testing assembly 30 may attach directly to an engine component, e.g. by clipping onto the front and/or rear of a single High Pressure compressor stage (as shown in FIG. 2) or into the shroud grooves of an Intermediate Pressure compressor drum assembly (as shown in FIG. 3). However, the erosion testing assembly 30 may be applied to any component with an erosion resistant surface. The erosion testing assembly may also be applied to any component for which the remaining erosion life would be of interest. Such components may include compressor and fan blades with erosion resistant surfaces.

The connector 70 may be configured to fit a specific component to ensure a good seal and accurate aligning of the erosion test area on the abradable surface 62. The erosion testing assembly 30 may attach to the component 60 in such a manner that the erosion grit is focused in a direction towards the abradable surface 62. Furthermore, the area outside of a test region on the component 70 may be shielded by the shroud 32 and the seal between the connector 70 and the component 60. The size of the test region may therefore be limited and damage to the remainder of the component and device may be prevented.

The profile measurement device 80 may measure the degree of erosion damage to the abradable surface 62. For example, the profile measurement device 80 may measure the erosion damage after the component has been used in its intended application for a period of time. The profile measurement device 80 may measure the profile of the abradable surface 62 prior to erosion testing. The erosion gun 50 may then replace the profile measurement device 80 and the erosion test may be undertaken. The profile measurement device 80 may then be reattached to measure the extent of further erosion. Alternatively, the pre and post test profile may be measured with a 3D profiler, e.g. an optical 3D profiler, and/or the profile may be compared with a standard replica. Furthermore, a calibration standard may be fixed directly in front of the abradable lining 62 to calibrate the erosion testing assembly 30. The calibration standard may comprise a PMMA (Perspex®) blank.

The erosion testing assembly of the present disclosure may be used on a relatively small area of the component, for example to avoid unduly affecting the performance of the remainder of the component. The abradable surface may be reapplied to the tested area. Different areas of the component may be tested on subsequent tests. The performance of the abradable surface may be monitored and compared against known benchmarks for the abradable surface.

The invention claimed is:

1. A method of measuring the erosion performance of a surface of a component, wherein the method comprises the steps of:
   a) attaching a shroud to the component;
   b) connecting an erosion gun to the shroud;
   c) performing an erosion test by eroding the surface with the erosion gun;
   d) replacing the erosion gun with a profile measuring device connected to the shroud; and
   e) measuring a post-test profile of the surface to determine the degree of erosion damage thereto.

2. The method of claim 1, wherein the method further comprises before step b) the steps of:
   aa) connecting a profile measuring device to the shroud;
   ab) measuring a pre-test profile of the surface to determine its condition;
   ac) removing the profile measuring device from the shroud;
   using the component; and
   testing a portion of the surface after use of the component.

3. The method of claim 2, wherein the method further comprises after step e) the step of:
   ea) comparing the post-test profile to the pre-test profile.

* * * * *